US007507208B2

(12) United States Patent
Bennett et al.

(10) Patent No.: US 7,507,208 B2
(45) Date of Patent: Mar. 24, 2009

(54) METHOD AND APPARATUS FOR CONTINUOUS PULSE CONTOUR CARDIAC OUTPUT

(75) Inventors: Tommy D. Bennett, Shoreview, MN (US); Robert T. Taepke, II, Coon Rapids, MN (US); Barbro M. Kjellstrom, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/124,847

(22) Filed: May 21, 2008

(65) Prior Publication Data

US 2008/0243006 A1 Oct. 2, 2008

Related U.S. Application Data

(63) Continuation of application No. 11/045,573, filed on Jan. 27, 2005, now abandoned.

(51) Int. Cl.
*A61B 5/00* (2006.01)

(52) U.S. Cl. .................. 600/485; 600/490; 600/500

(58) Field of Classification Search .............. None
See application file for complete search history.

(56) References Cited

U.S. PATENT DOCUMENTS

| 5,241,966 A | 9/1993 | Finkelstein et al. |
| 5,265,615 A | 11/1993 | Frank et al. |
| 5,400,793 A | 3/1995 | Wesseling |
| 5,797,395 A | 8/1998 | Martin |
| 6,071,244 A | 6/2000 | Band et al. |
| 6,073,048 A | 6/2000 | Kieval et al. |
| 6,167,412 A | 12/2000 | Simons et al. |
| 6,314,323 B1 | 11/2001 | Ekwall |
| 6,394,958 B1 | 5/2002 | Bratteli et al. |
| 6,865,419 B2 | 3/2005 | Mulligan et al. |
| 2002/0103442 A1 | 8/2002 | Mulligan et al. |
| 2003/0199779 A1 | 10/2003 | Muhlenberg et al. |
| 2004/0167410 A1 | 8/2004 | Hettrick |

OTHER PUBLICATIONS

International Search Report, PCT/US2006/002989, Jul. 19, 2007, 4 pages.
European Communication, EP 06719714.5, Jul. 8, 2008, 6 pages.

*Primary Examiner*—Robert L Nasser
(74) *Attorney, Agent, or Firm*—Reed A. Duthler

(57) ABSTRACT

A system and method are provided for sensing cardiac electrogram (EGM) signals and ventricular pressure signals and for using the sensed EGM and sensed pressure signals for estimating stroke volume (SV). A measure of cardiac output can be computed from the estimated SV and a heart rate determined from the EGM signals. The sensed ventricular pressure signal and the sensed EGM signal are used to derive landmark points such as an estimated pulmonary diastolic pressure, a mean pulmonary artery pressure, a peak right ventricular pressure (RVP), and various time intervals used in computing an area or a pulse contour integral. The pulse contour integral is used to estimate SV. The estimated pulmonary diastolic pressure, mean pulmonary artery pressure and CO computed from the estimated SV can be used to compute a pulmonary vascular resistance.

14 Claims, 13 Drawing Sheets

METHOD AND APPARATUS FOR CONTINUOUS PULSE CONTOUR CARDIAC OUTPUT

CROSS REFERENCE TO PRIORITY APPLICATION

This application is a continuation of U.S. patent application Ser. No. 11/045,573, filed Jan. 27, 2005 now abandoned, which is incorporated by reference herein.

FIELD OF THE INVENTION

The present invention relates generally to: hemodynamic monitoring devices and methods and particularly to a method and apparatus for monitoring cardiac output using ventricular pressure signals,

BACKGROUND OF THE INVENTION

Implantable hemodynamic monitors are available for monitoring fight ventricular pressure chronically in an ambulatory patient. Patients with congestive heart failure (CHF) have elevated cardiac filling pressures and reduced cardiac output. A major treatment objective is to lower filling pressures while maintaining adequate cardiac output. Therefore, from a hemodynamic monitoring perspective, it is advantageous to monitor both filling pressures and measures of cardiac output.

BRIEF SUMMARY OF THE INVENTION

The present invention provides a system and method for monitoring cardiac output estimated from a ventricular pressure signal using pulse contour analysis. In one embodiment, the right ventricular pressure (RVP) signal is acquired from an implantable pressure sensor deployed in the right ventricle. The RVP contour is analyzed to estimate stroke volume (SV) during cardiac systole, from which an estimate of forward flow can be derived.

The system includes a pressure sensor adapted for implantation in the right ventricular chamber for sensing the RVP signal. The system may optionally include an electrode for measuring cardiac electrical signals, such as an intracardiac electrogram (EGM). The electrode and pressure sensor are coupled to an implantable cardiac monitoring device including signal recovery circuitry, processing circuitry, and associated memory for acquiring and storing heart rate (from the EGM) and RVP signal information. The RVP signals are processed by the microprocessor to estimate SV on a beat-by-beat basis when cardiac output monitoring is enabled. The implantable cardiac monitoring device is equipped with telemetry circuitry for communicating with an external programmer. RVP data or estimated SV data in digital units along with heart rate and any other relevant data may be uplinked to the external programmer and further processed by a microprocessor included in the external programmer or transferred to another computer for computing an actual flow value using patient-specific calibration, In an associated method: for estimating SV from the RVP signal, landmark points are identified on the RVP contour during the systolic time interval, the start of the systolic time interval is identified by detecting an R-wave event. An analysis window is set upon detecting an R-wave event. The analysis window duration is a predetermined interval set to include the systolic time interval. The RVP signal is acquired and stored in a memory buffer during the analysis window to allow identification of landmark points and computation of the estimated SV.

In one embodiment, the landmark points identified for use in computing an estimated SV are the peak RVP and the estimated pulmonary artery diastolic (ePAD) pressure, which is equal to the RVP signal amplitude at the time of the maximum rate of rise in RVP (dP/dt max). A measure of estimated SV is computed as the difference between peak RVP and ePAD.

In another embodiment, the area under the pressure pulse is approximated using polygonal (e.g. triangular, rectangular, or trapezoidal) shapes whose vertices or sides are defined by various landmarks of the RVP pulse. The vertices and sides of the polygons can be defined by the values or times of occurrence of dP/dt max, dP/dt min, a single global or multiple local pressure peaks during systole, ePAD, RVP at dP/dt min, RVP where the descending RVP contour equals the mean PA pressure, and inflection points between multiple local peaks that sometimes occur on the RVP waveform. There may be other landmarks on the RVP waveform that are useful, besides those listed above.

In yet another embodiment, a pulse contour integral is computed as an estimate of SV. Landmark points are identified on the RVP signal for use as an integration start time and an integration end time. The integration start time corresponds to the start of the systolic ejection interval which is marked by the opening of the pulmonic valve. In one embodiment, integration start time is identified as the time of dP/dt max or ePAD. The integration end time corresponds to the end of the systolic ejection interval, marked by closure of the pulmonic valve. In one embodiment, integration end time is identified as the time that the descending RVP contour equals ePAD. An area defined by the RVP contour during the integration time interval is computed and may be used to derive an estimate of SV.

In some embodiments, the estimated SV computed as the area under the RVP contour during the integration time interval is corrected by a number of correction areas. Correction areas are computed based on landmark points on the RV pressure signal. Correction areas are used to compute a pulse contour integral (PCI) that more accurately represents the pulmonary artery flow contour and accordingly provides a more accurate estimate of SV.

An estimated SV can be used to compute a measure of cardiac output (CO) by dividing the estimated SV by the R-R interval (RRI) on a beat-by-beat basis. The estimated SV and CO will be in digital units. These digital values may be used by the IMD in closed loop control methods for managing device-delivered therapies. SV and CO estimates computed in digital units may be uplinked to an external device and converted to actual volume and flow units using patient-specific calibration values.

In some embodiments, additional hemodynamic monitoring parameters are estimated from the right ventricular pressure signal including mean pulmonary artery pressure (MPAP) and pulmonary vascular resistance (PVR) to provide a set of meaningful hemodynamic diagnostics for use in managing cardiac disease.

Practice of the present invention for estimating stroke volume and cardiac output from a ventricular pressure signal is not limited to using the RVP signal. Use of the RVP signal allows estimation of pulmonary artery pressures at various time points in the cardiac cycle which further allows estimation of flow. However, a left ventricular pressure (LVP) signal may be obtained for use in estimating aortic pressures at various time points in the cardiac cycle which may be further used for estimating flow. Since flow from the left and right ventricles is equal over time, estimation of cardiac output from either left or right ventricular pressure signals can be used. As such, various embodiments of the present invention include approximating an estimated stroke volume as an area under the left ventricular pressure pulse using polygonal shapes whose vertices or sides are defined by various landmarks of the LVP pulse, or computing a pulse contour integral as an estimate of SV based on an integration start time and an integration end time derived from landmark points on the LVP signal.

DETAILED DESCRIPTION

Figure 1:
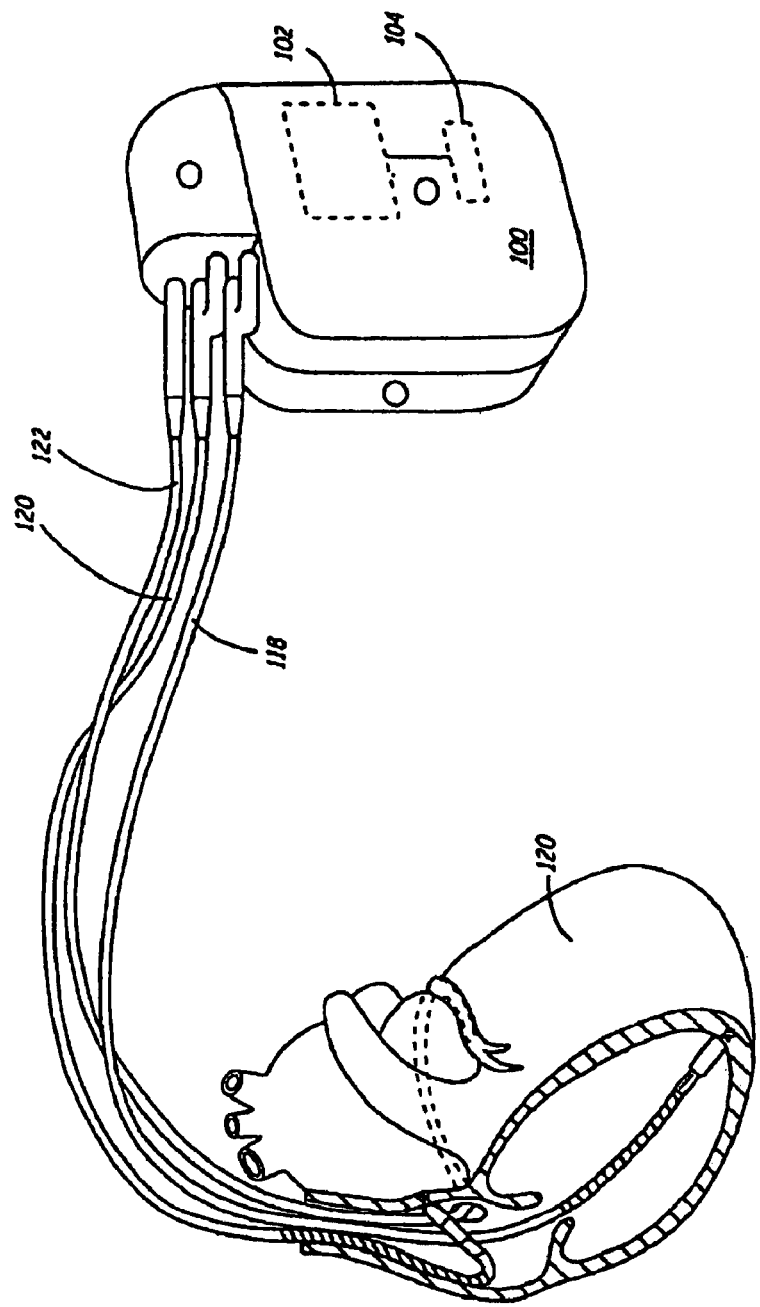
FIG. 1 is an illustration of an exemplary implantable medical device (IMD) configured to monitor a patient's heart.

FIG. 1 is an illustration of an exemplary implantable medical device (IMD) 100 connected to monitor a patient's heart 120. IMD 100 may be configured to integrate both monitoring and therapy features, as will be described below. IMD 100 collects and processes data about heart 120 from one or more sensors including a pressure sensor and an electrode for sensing cardiac electrogram (EGM) signals. IMD 100 may further provide therapy or other response to the patient as appropriate, and as described more fully below. As shown in FIG. 1 IMD 100 may be generally flat and thin to permit subcutaneous implantation within a human body, e.g., within upper thoracic regions or the lower abdominal region. IMD 100 is provided with a hermetically-sealed housing that encloses a processor 102, a digital memory 104, and other components as appropriate to produce the desired functionalities of the device. In various embodiments, IMD 100 is implemented as any implanted medical device capable of measuring the heart rate of a patient and a ventricular pressure signal, including, but not limited to a pacemaker, defibrillator, electrocardiogram monitor, blood pressure monitor, drug pump, insulin monitor, or neurostimulator. An example of a suitable IMD that may be used in various exemplary embodiments is the CHRONICLE® monitoring device available from Medtronic, Inc. of Minneapolis, Minn., which includes a mechanical sensor capable of detecting a ventricular pressure signal. In a further embodiment, IMD 100 is any device that is capable of sensing ventricular pressure and providing pacing and/or defibrillation to the heart. Another example of an IMD capable of sensing pressure-related parameters is described in commonly assigned U.S. Pat. No. 6,438,408B1 issued to Mulligan et al. on Aug. 20, 2002.

Processor 102 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 102 executes instructions stored in digital memory 104 to provide functionality as described below. Instructions provided to processor 102 may be executed in any manner, using any data structures, architecture, programming language and/or other techniques. Digital memory 104 is any storage medium capable of maintaining digital data and instructions provided to processor 102 such as a static or dynamic random access memory (RAM), or any other electronic, magnetic, optical or other storage medium.

As further shown in FIG. 1, IMD 100 may receive one or more cardiac leads for connection to circuitry enclosed within the housing. In the example of FIG. 1, IMD 100 receives a right ventricular endocardial lead 118, a left ventricular coronary sinus lead 122, and a right atrial endocardial lead 120, although the particular cardiac leads used will vary from embodiment to embodiment. In addition, the housing of IMD 100 may function as an electrode, along with other electrodes that may be provided at various locations on the housing of IMD 100. In alternate embodiments, other data inputs, leads, electrodes and the like may be provided. Ventricular leads 118 and 122 may include, for example, pacing electrodes and defibrillation coil electrodes (not shown) in the event IMD 100 is configured to provide pacing, cardioversion and/or defibrillation. In addition, ventricular leads 118 and 122 may deliver pacing stimuli in a coordinated fashion to provide biventricular pacing, cardiac resynchronization, extra systolic stimulation therapy or other benefits. IMD 100 obtains pressure data input from a pressure sensor that is carried by a lead shown in FIG. 1, such as right ventricular endocardial lead 118. A pressure sensor may alternatively be located on an independent lead provided for deployment of the pressure sensor in the right or left ventricle for obtaining a ventricular pressure signal. IMD 100 may also obtain input data from other internal or external sources (not shown) such as an oxygen sensor, pH monitor, arterial pressure sensor, accelerometer or the like.

In operation, IMD 100 obtains data about heart 120 via leads 118, 120, 122, and/or other sources. This data is provided to processor 102, which suitably analyzes the data, stores appropriate data in memory 104, and/or provides a response or report as appropriate. Any identified cardiac episodes (e.g. an arrhythmia or heart failure decompensation) can be treated by intervention of a physician or in an automated manner. In various embodiments, IMD 100 activates an alarm upon detection of a cardiac event. Alternatively or in addition to alarm activation, IMD 100 selects or adjusts a therapy and coordinates the delivery of the therapy by IMD 100 or another appropriate device. Optional therapies that may be applied in various embodiments may include drug delivery or electrical stimulation therapies such as cardiac pacing, resynchronization therapy, extra systolic stimulation, neurostimulation, or modifications in drug delivery or electrical stimulation parameters.

Figure 2:
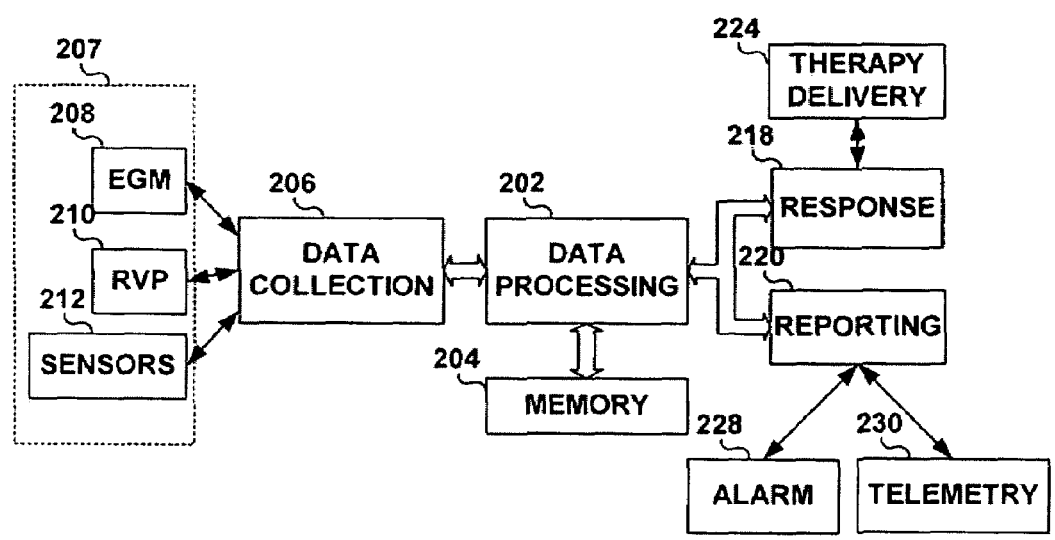
FIG. 2 is a block diagram summarizing the data acquisition and processing functions for the IMD shown in FIG. 1.

FIG. 2 is a block diagram summarizing the data acquisition and processing functions for IMD 100. IMD 100 includes a data collection module 206, a data processing module 202, a response module 218 and/or a reporting module 220. Each of the various modules may be implemented with computer-executable instructions stored in memory 104 and executing on processor 102 (shown in FIG. 1), or in any other manner. The exemplary modules and blocks shown in FIG. 2 are intended to illustrate one logical model for implementing an IMD 100 for monitoring cardiac output using ventricular pressure signals, and should not be construed as limiting. Indeed, the various practical embodiments may have widely varying software modules, data structures, applications, processes and the like. As such, the various functions of each module may in practice be combined, distributed or otherwise differently-organized in any fashion in or across an IMD system that includes implantable sensors, an IMD and an external programmer.

Data collection module 206 is interfaced with one or more data sources 207 to obtain data about the patient. Data sources 207 include any source of information about the patient's heart or other physiological signals. Data sources 207 include an ECG or EGM source 208 that provides cardiac electrical signals such as P-waves or R-waves used to monitor the patient's heart rhythm. Data sources 207 further include a ventricular pressure sensor 210 for obtaining a pressure signal from which cardiac output may be estimated using pulse contour analysis methods as will be described in detail below. Data sources 207 may include other sensors 212 for acquiring physiological signals useful in monitoring a cardiac condition such as an accelerometer or wall motion sensor, a blood gas sensor such as an oxygen sensor, a pH sensor, or impedance sensors for impedance changes relating to respiration, lung wetness, or cardiac chamber volumes. The various data sources 207 may be provided alone or in combination with each other, and may vary from embodiment to embodiment Pressure sensor 210 may be embodied as the pressure sensor disclosed in commonly assigned U.S. Pat. No. 5,564,434, issued to Halperin et al., hereby incorporated herein in its entirety.

Data collection module 206 receives data from each of the data sources 207 by polling each of the sources 207, by responding to interrupts or other signals generated by the sources 207, by receiving data at regular time intervals, or according to any other temporal scheme. Data may be received at data collection module 206 in digital or analog format according to any protocol. If any of the data sources generate analog data, data collection module 206 translates the analog signals to digital equivalents using an analog-to-digital conversion scheme. Data collection module 206 may also convert data from protocols used by data sources 207 to data formats acceptable to data processing module 202, as appropriate.

Data processing module 202 is any circuit, programming routine, application or other hardware/software module that is capable of processing data received from data collection module 206. In various embodiments, data processing module 202 is a software application executing on processor 102 (FIG. 1) to implement the processes described below for estimating SV from a ventricular pressure signal. Accordingly, data processing module 202 processes ventricular pressure signals for computing an estimated SV which may further be used for determining a measure of cardiac output, as described more fully below.

In an exemplary embodiment, processing module 202 receives data from ventricular pressure sensor 210 and EGM data from EGM sensing electrodes 208 from data collection module 206 and interprets the data using digital signal processing techniques to compute an estimated stroke volume (in digital units) on a beat-by-beat basis. The stroke volume is the volume of blood ejected from the ventricle during a cardiac systole. An estimated flow (CO) can be computed from the estimated stroke volume and a measure of the heart rate. The estimated CO and/or intermediate computational results may be stored in memory 204, which may correspond to hardware memory 104 shown in FIG. 1, or may be-implemented with any other available digital storage device. CO monitoring data may be acquired and stored on a scheduled or triggered basis to allow trends in CO to be monitored for use in managing the hemodynamic status of the patient.

When a change in CO based on the estimated SV is detected, processing module 202 may trigger an appropriate response. Responses may be activated by sending a digital message in the form of a signal, passed parameter or the like to response module 218 and/or reporting module 220.

Reporting module 220 is any circuit or routine capable of producing appropriate feedback from the IMD to the patient or to a physician. In various embodiments, suitable reports might include storing data in memory 204, generating an audible or visible alarm 228, producing a wireless message transmitted from a telemetry circuit 230. Reports may include information about the estimated stroke volume, cardiac output, pressure measurements derived from the right ventricular pressure signal, heart rhythm, time and date of data collection, and any other appropriate data. In a further embodiment, the particular response provided by reporting module 220 may vary depending upon the severity of the hemodynamic change. Minor episodes may result in no alarm at all, for example, or a relatively non-obtrusive visual or audible alarm. More severe episodes might result in a more noticeable alarm and/or an automatic therapy response.

Telemetry circuitry 230 communicates data from IMD 100 to an external device adapted for bidirectional telemetric communication with IMD 100. The external device receiving the wireless message may be a programmer/output device that advises the patient, a physician or other attendant of serious conditions, e.g., via a display or a visible or audible alarm. Information stored in memory 204 may be provided to an external device to aid in diagnosis or treatment of the patient. Alternatively, the external device may be an interface to a communications network such that IMD 100 is able to transfer data to an expert patient management center or automatically notify medical personnel if an extreme episode occurs.

Response module 218 is any circuit, software application or other component that interacts with any type of therapy-providing system 224, which may include, any type of therapy delivery mechanisms such as a drug delivery system 222, neurostimulation 226 and/or cardiac stimulation 224. In some embodiments, response module 218 may alternatively or additionally interact with an electrical stimulation therapy device integrated with IMD 100 to deliver pacing, cardiac resynchronization therapy, extra systolic stimulation, cardioversion, defibrillation and/or any other therapy. Accordingly, the various responses that may be provided by IMD 100 vary from simple storage of data to actual provision of therapy in various embodiments. Any therapy provided may be controlled or adjusted in response to a hemodynamic change observed as a change in stroke volume or cardiac output estimated from a right ventricular pressure signal or in response to a combination of physiological signals acquired by data sources 207. Drug dosage may be adjusted according to episode severity, for example, or electrical stimulation parameters can be adjusted in response to observed deterioration in hemodynamic measures.

The various components and processing modules of IMD 100 may be housed in a common housing such as that shown in FIG. 1. Alternatively, portions of IMD 100 may be housed separately. For example, portions of the therapy delivery system 224 could be integrated with IMD 100 or provided in a separate housing, particularly where the therapy delivery system includes drug delivery capabilities. In this case, response module 218 may interact with therapy delivery system 224 via an electrical cable or wireless link.

Figure 3:
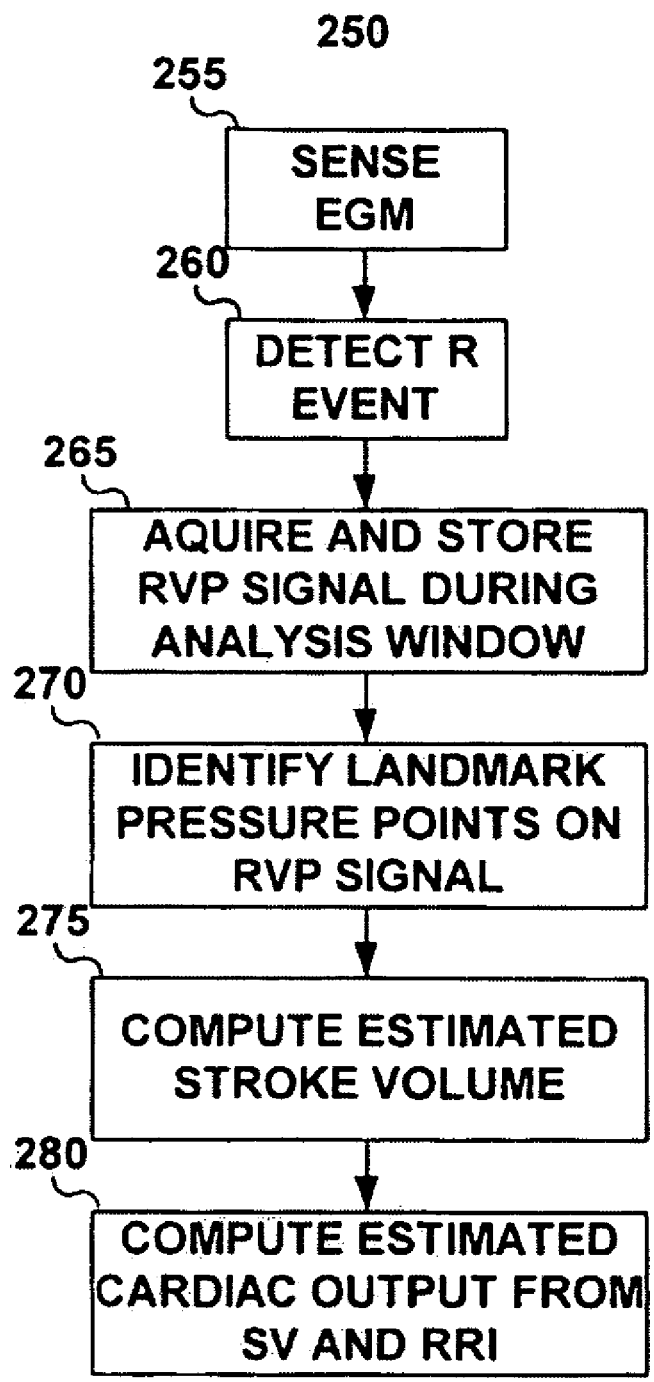
FIG. 3 is a flow chart summarizing a method for computing an estimated SV from a right ventricular pressure signal for use in CO monitoring.

FIG. 3 is a flow chart summarizing a method 300 for computing an estimated SV from a right ventricular pressure signal for use in CO monitoring. The steps shown in the flow chart of FIG. 3, as well as the other flow charts presented herein, may be implemented within an IMD, such as the IMD shown in FIG. 1, or across an IMD system or patient management system. Generally, the EGM and RVP signals will be acquired by an IMD and initially processed to obtain beat-by-beat SV estimates in digital units along with associated heart rate data, which may be used to compute CO in digital units. The digital estimated SV and heart rate data can be uplinked to an external programmer or monitor for further processing to determine CO in physical units of L/min.

Cardiac output monitoring may be enabled upon detecting a predetermined triggering event, on a scheduled basis, or manually by a clinician, patient or other caregiver using an external device. When cardiac output monitoring is enabled, the EGM signal is sensed at step 255 to allow detection of the onset of a cardiac cycle based on a detected R-wave event at step 260; A detected R-wave event may be an R-wave detected oh an EGM signal but could alternatively be a pacing event or other electrical signal appropriate for marking the start of a cardiac cycle. The present invention is hot limited, however, to the use of an EGM signal or pacing signal for detecting the start of a cardiac cycle. Other physiological signals could be substituted from which an approximation of the start of the cardiac cycle may be made. In one alternative embodiment, a pressure/signal may be used to detect the start of the cardiac cycle. For example, a predetermined threshold crossing of pressure amplitude or dP/dt determined from the RVP signal (or another pressure signal) may be detected as an R-wave related event and used as the starting point of a cardiac cycle for the purposes of the present invention.

Once an R-wave event is detected at step 260, the RVP signal is acquired for a predetermined interval of time, or analysis window, during which analysis of the RVP signal will be performed for estimating stroke volume. The RVP signal data is stored in a memory buffer to allow the signal to be analyzed. In one embodiment, RVP signal data is stored in a memory buffer for about 500 msec following an R-wave event detection. Anomalous cardiac cycles associated with arrhythmias, premature contractions, or noise may be rejected.

At step 270, a number of landmark features or points are identified on the RVP signal during the analysis window. As will be described in detail below, the amplitude of the RVP at the landmark points and/or the time of the landmark points relative to the R-wave event detection will be used for computing an estimated stroke volume at step 275. The CO can then be computed at step 280 from the estimated SV and the heart rate determined from intervals between successive R-wave events. The CO may be computed on a beat-by-beat basis or may be calculated over an interval of time for which the heart rate and an averaged estimated SV is determined.

Data processing circuitry 202 (in FIG. 2) within the IMD may be used to compute the estimated CO in digital units at step 280. The estimated CO may be computed on a beat-by-beat or interval basis allowing trends in CO to be determined by data processing circuitry 202. Changes in estimated CO detected by data processing circuitry 202 can be responded to appropriately by response module 218 (FIG. 2). Thus, estimated CO may be used in a closed-loop control algorithm for controlling therapy delivery. Estimated CO data may additionally or alternatively be stored in IMD memory for uplinking to an external device for review and analysis by a clinician.

After uplinking to an external device, the estimated SV in digital units may be converted to physical units of volume such that CO may be determined in units of volume per unit time. The estimated SV is converted to units of volume by multiplying by a calibration gain and/or adding a calibration offset value. The calibration values are determined for a given pressure sensor and may be individualized for a given patient. In some embodiments, non-linear calibration factors may be used for converting estimated SV values to actual values in volume units. If method 300 is fully implemented in an IMD, calibration factors may be downlinked to the IMD for performing conversion of SV and/or CO data from digital to physical units.

Figure 4:
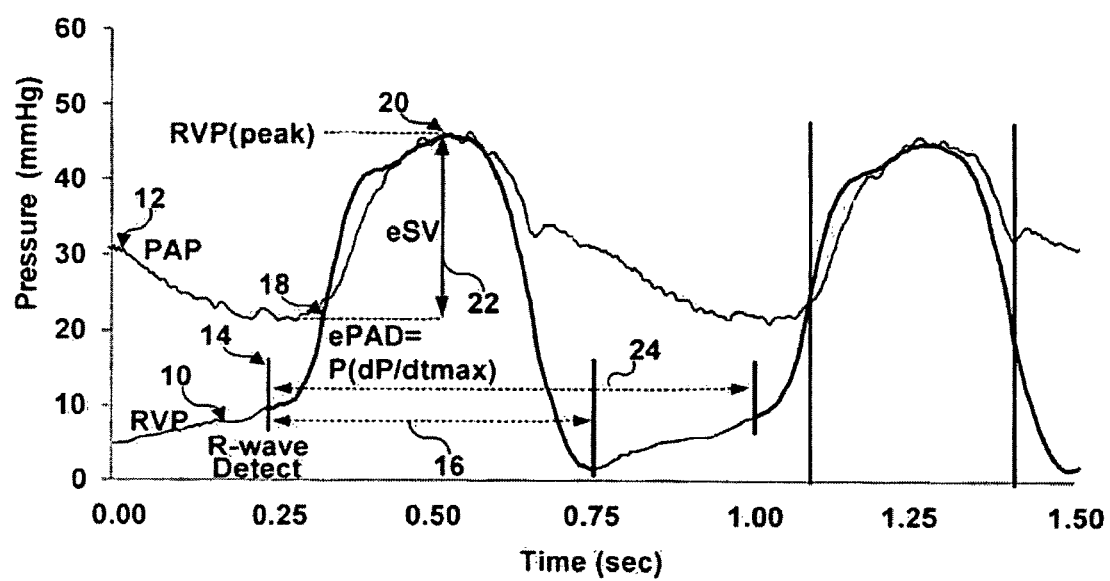
FIG. 4 shows a RVP signal and illustrates one method for estimating SV from the RVP signal.

FIG. 4 shows a RVP signal and illustrates one method for estimating SV from the RVP signal. A recording of a RVP signal 10 is shown over a period of approximately two cardiac cycles. The RVP signal 10 is shown superimposed on a pulmonary artery pressure signal 12 for the purpose of illustrating the usefulness of landmark pressure points determined from a RVP signal in estimating SV. Ejection of blood from the right ventricle increases flow and pressure in the pulmonary artery. Estimation of flow from arterial signals using pulse contour analysis is useful in monitoring a patient's cardiac output. The use of arterial pressure waveforms for monitoring CO using pulse contour cardiac output techniques are known in the art. In the present invention, the RVP signal is analyzed to determine landmark pressure points that correlate to events in the pulmonary artery pressure signal and are therefore useful in estimating stroke volume in a modified pressure pulse contour analysis approach.

The pulmonic valve opens when pressure within the right ventricle exceeds the pulmonary artery diastolic pressure. Blood is then ejected from the right ventricle and forward flow occurs. The pulmonary artery diastolic (PAD) pressure can be estimated as being equal to the pressure in the right ventricle at the time that the maximum rate of pressure rise, dP/dtmax, occurs in the right ventricle. Methods for deriving ePAD from a ventricular pressure signal are generally disclosed in U.S. Pat. No. 5,368,040 issued to Carney, U.S. Pat. No. 5,626,623 issued to Kieval et al., and U.S. Pat. No. 6,580,946 B2 issued to Struble, all of which patents are hereby incorporated herein in their entirety.

In accordance with the method described above in conjunction with FIG. 3, a RVP signal analysis window 16 is applied upon detection of an R-wave event 14. The RVP signal 10 is stored during window 16 to allow an analysis of the systolic portion of the RVP signal. During this analysis window, the RVP amplitude at the time of dP/dtmax is determined as the estimated PAD (ePAD) 18. The peak RV systolic pressure, RVP(peak), 20 is also determined during the analysis window 16. The difference between the RVP(peak) 20 and ePAD 18 can be determined as an estimated stroke volume (eSV) 22. This method for estimating SV assumes that the RV pressure generated following opening of the pulmonic valve is correlated to forward flow. The estimated SV based on the pressure difference during the ejection phase does not take into account variations in vascular impedance or the ejection interval but may provide a useful measure for monitoring CO.

An estimated CO can be computed from the estimated SV by dividing the eSV by the RRI 24 measured for the current cardiac cycle. If desired, the estimated CO can be converted later to units of volume per unit time using calibration factors as described above.

Figure 5:
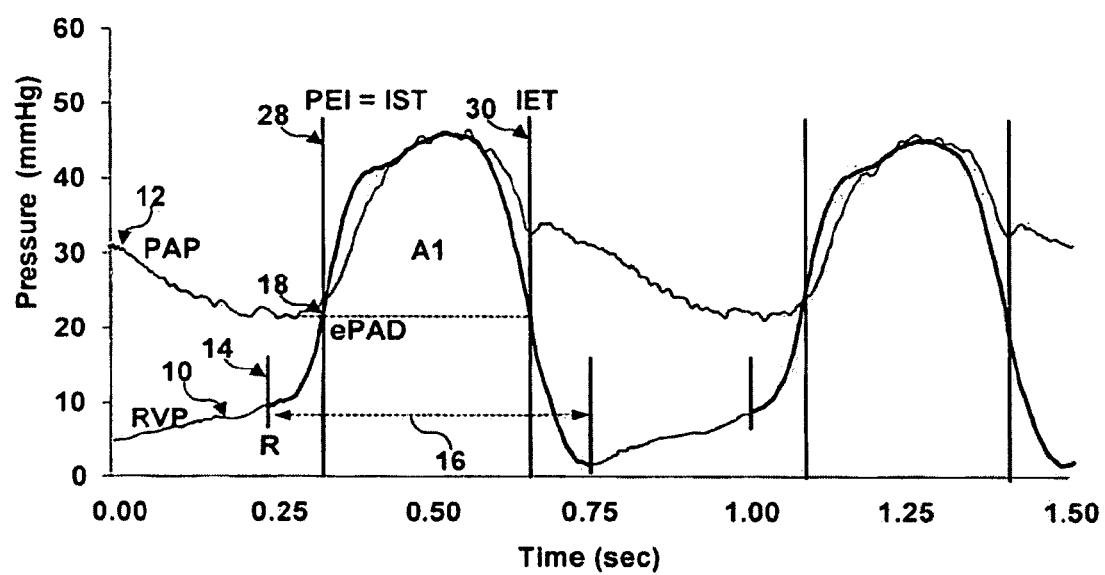
FIG. 5 illustrates a method for determining an integration interval for use in computing a pressure pulse contour integral in an alternative method for estimating SV from the RVP signal.

FIGS. 5 through 9 illustrate another method for computing an estimated SV using pulse contour analysis of the RVP signal. FIG. 5 illustrates a method for determining an integration interval for use in computing a pressure pulse contour integral. Following detection of an R-wave event 14, the RVP signal 10 is acquired and stored over a predetermined analysis window 16 to allow landmark points to be determined from the systolic portion of the RVP signal. The time at which the maximum rate of RVP rise (dP/dtmax) occurs, which corresponds to the ePAD 18, is determined as an integration start time (IST) 28. This integration start time 28 approximates the end of the pre-ejection interval (PEI) and the time of pulmonic valve opening, which marks the start of forward flow from the right ventricle.

An integration end time (IET) 30 is defined as the time at which the decreasing RVP signal amplitude equals the ePAD 18. The time at which the RVP equals the ePAD 18 is one approach to approximating the time of pulmonic valve closure, which marks the end of forward flow from the right ventricle. The area A1 under the RVP signal 10 between the integration start time 28 and integration end time 30 is computed. This area A1 will be used in computing an estimated stroke volume as will be further described below.

In one embodiment, the area A1, bounded by the RVP signal 10, the zero baseline, and the integration start time 28 and integration end time 30, may be used as an estimated stroke volume. However, this area A1 may overestimate the stroke volume due to inclusion of areas bounded by the RVP signal that do not correlate to actual forward flow from the right ventricle. FIGS. 6 through 9 illustrate the computation of correction areas that may be used for correcting the area A1 for determining a more accurate estimate of stroke volume.

Figure 6:
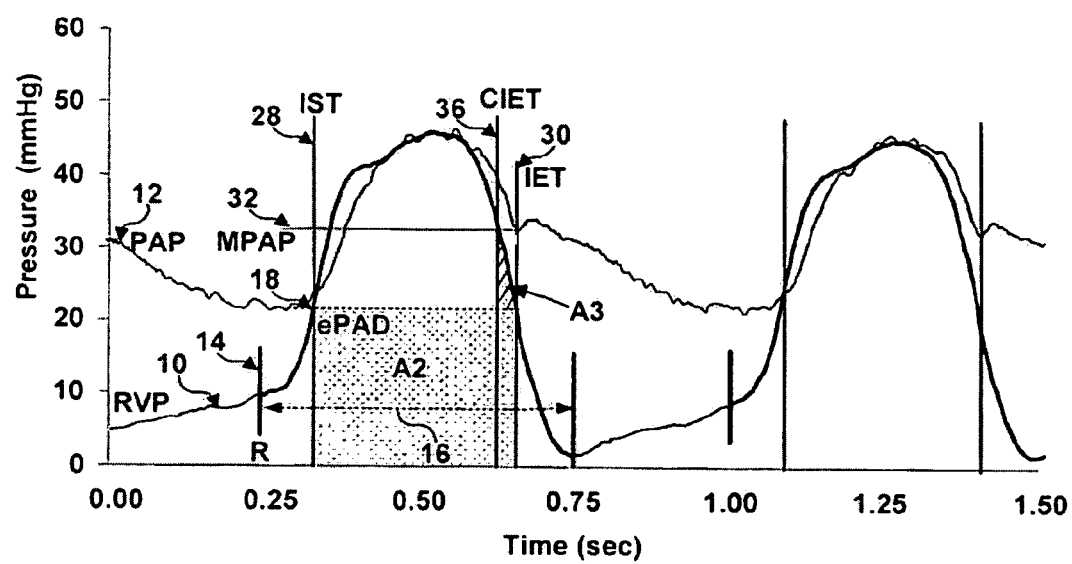
FIG. 6 illustrates a method for computing two correction areas, A2 and A3, used in calculating a RVP pulse contour integral for estimating SV.

In FIG. 6, area A2 is defined as the area bounded by ePAD 18 and the zero baseline between the integration start time 28 and integration end time 30. Area A2 can be thought of as area related to pressure generated during the pre-ejection interval that does not contribute to forward flow. Area A2 may be subtracted from area A1 to provide a more accurate estimated stroke volume.

The accuracy of the estimated SV computed from the RVP contour will depend in part on the accuracy of the estimated time of valve opening and closure. If the integration end time 30 occurs after pulmonic valve closure, the area under the RVP signal calculated as an estimate of SV may overestimate the SV. The pulmonary artery pressure at the time of valve closure may be closer to the mean pulmonary artery pressure during a cardiac cycle rather than the ePAD. Hence, the time of pulmonic valve closure may be more accurately estimated as the time at which the RVP signal amplitude equals the mean pulmonary artery pressure (MPAP). MPAP may be estimated from the RVP signal according to methods generally disclosed in U.S. patent application Ser. No. 09/997,753, filed Nov. 30, 2001, hereby incorporated herein in its entirety.

Figure 7:
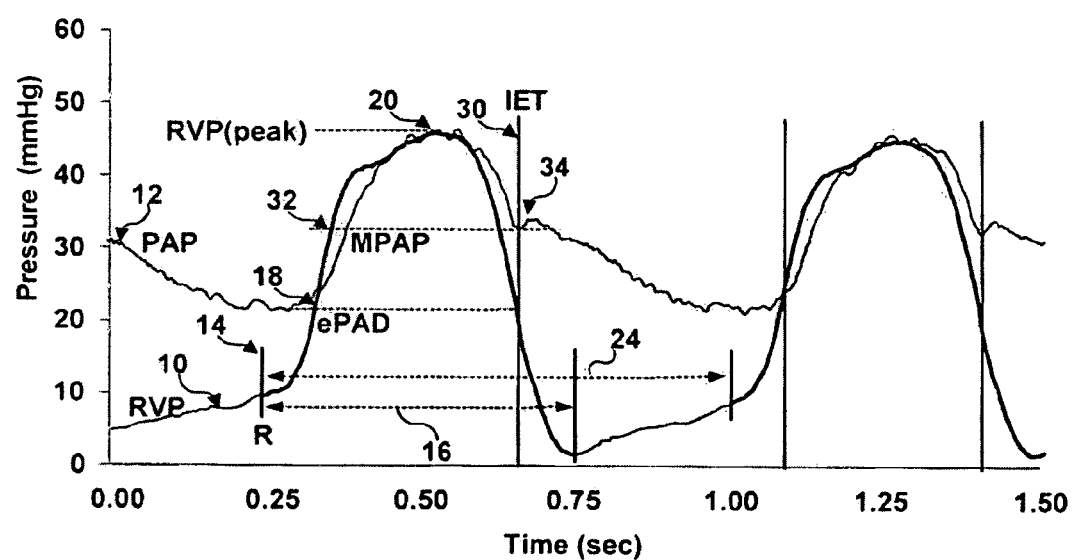
FIG. 7 illustrates a method for computing an estimated mean pulmonary artery pressure from the RVP signal.

FIG. 7 illustrates a method for computing an estimated mean pulmonary artery pressure from the RVP signal. The pulmonic valve closes at the time of the dicrotic notch 34 in the PAP waveform 12. The corresponding MPAP is computed as a weighted average of the peak RVP 20 and ePAD 18. Weighting factors are determined from the systolic and diastolic time intervals measured during the cardiac cycle. A ratio of the systolic time interval (STI) to the total RRI is used as the peak RVP weighting factor. The STI can be measured as the time interval beginning at R-wave event detection 14 and ending at the previously determined integration end time 30. The STI can be defined generally as an interval extending from a detection of the start of systole, such as R-wave event detection 13 to a detection of the end of systole, such as dP/dt$_{min}$. The ratio of the diastolic interval to the total RRI is used as the ePAD weighting factor. The diastolic interval can be determined as the difference between the RRI and the measured systolic time interval. Thus, the MPAP can be estimated from the RVP signal 10 according to the following equation {1}.

$$\text{MPAP} = \{\text{RVP(peak)} * (\text{STI/RRI})\} + \{\text{ePAD} * (\text{RRI-STI})/\text{RRI}\}. \quad \{1\}$$

Referring again to FIG. 6, the MPAP 32 computed according to the above equation can be used to identify a corrected integration end time (CIET) 36. The time at which pulmonic valve closure occurs, i.e. the time at which forward flow ends, may be more accurately estimated on the RVP curve 10 as the time at which the descending RVP signal amplitude equals the estimated MPAP 32. The area A3 under the RVP signal 10 and to the right of the corrected integration end time 36 may cause the SV computed from area A1 to be overestimated. This area A3 may be approximated as a triangular area computed from the following equation {2}:

$$A3 = 0.5 * (\text{MPAP} - \text{ePAD}) * (\text{IET} - \text{CIET}) \quad \{2\}$$

In some embodiments, the correction area A3 is subtracted from the entire area A1 under the RVP signal 10 for estimating the SV more accurately.

Figure 8:
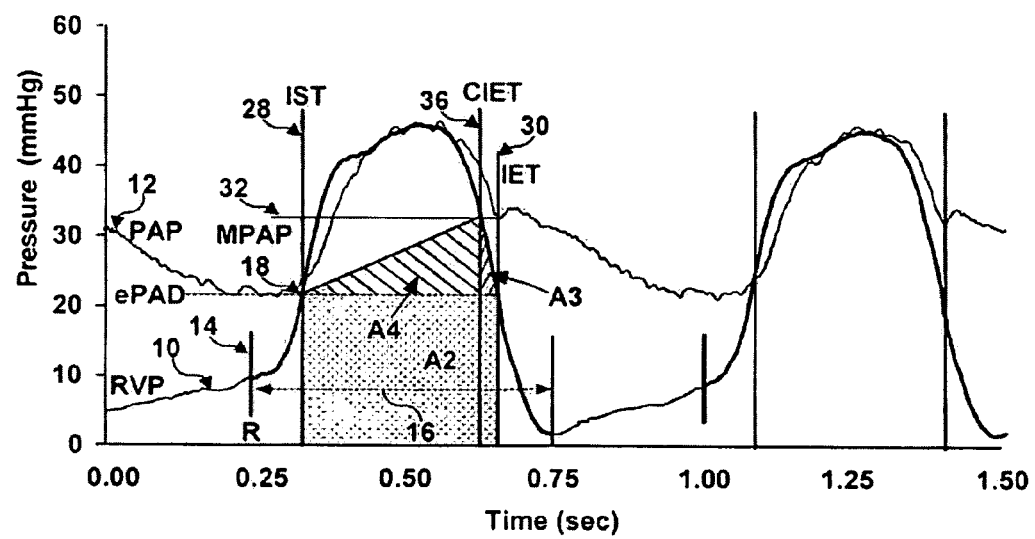
FIG. 8 illustrates the computation of a third correction area, A4, that may be used in computing a RVP pulse contour integral for estimating SV computed.

FIG. 8 illustrates the computation of a third area A4 that may be used to correct an estimated SV computed using the total integrated area A1 under the RVP waveform 10. The correction area A4 is approximated as a triangle and computed from the following equation {3}:

$$A4 = 0.5 * \{(\text{MPAP} - \text{ePAD}) * (\text{CIET} - \text{IST})\} \quad \{3\}$$

In some embodiments, the correction area A4 is subtracted from the entire area A1 under the RVP signal 10 for estimating the SV more accurately.

Figure 9:
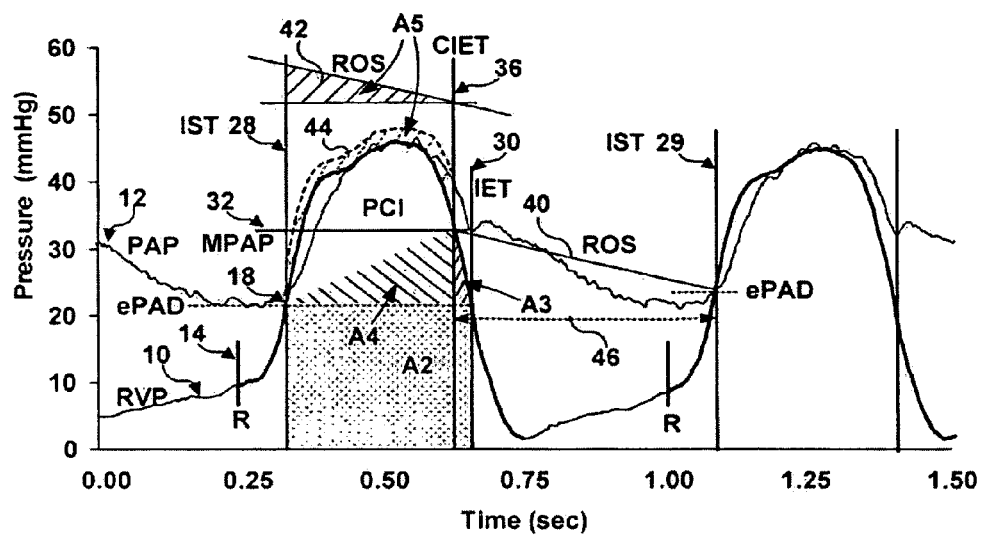
FIG. 9 illustrates the computation of a fourth correction area, A5, that may be used in computing a RVP pulse contour integrator estimating SV.

FIG. 9 illustrates the computation of a fourth correction area A5 that may be used to correct the total area A1, as an estimate of SV computed from the RVP waveform. Computation of an estimated SV from a RVP waveform can be limited in accuracy due to changes in pulmonary vascular resistance, or the load against which the ventricle must eject blood. Changes in pulmonary vascular resistance are not accounted for by pressure signal analysis alone. At least a portion of the pressure developed by the right ventricle contributes to overcoming pulmonary vascular resistance before producing forward flow. The effect of changes in pulmonary vascular resistance on SV may be corrected for by computing a fourth correction area A5. The area A5 is computed based on a "run-off slope."

The run-off slope (ROS) 40 is the slope between the MPAP 32 at the corrected integration end time 36 and ePAD 18 at the integration start time 29 of the next cardiac cycle. The run-off slope 40 represents the fall in pressure that occurs in the pulmonary vascular system after pulmonic valve closure occurs, prior to the start of the next ejection phase. In patients with high pulmonary vascular resistance, the pulmonary artery diastolic pressure will be high. A greater contribution of the generated RVP will be required to overcome the pulmonary vascular resistance before producing forward flow. When ePAD increases as a result of increased pulmonary vascular resistance, the run-off slope will decrease.

The run-off slope 40 is computed using equation {4}:

$$ROS=(MPAP-ePAD)/(RRI-CIET+IST) \quad \{4\}$$

The time interval 46 over which the run-off slope 40 is computed can be determined using time measurements (RRI, IST 28 and CIET 36) from the current cardiac cycle. Thus data regarding the subsequent cardiac cycle is not required for computing ROS 40. The time interval 46 can be computed as the RRI less the corrected integration end time 36 plus the integration start time 28 of the current cardiac cycle, rather than of the next cardiac cycle. The resulting time interval is approximately the interval of time 46 between pulmonic valve closure and pulmonic valve opening. Likewise, in computing the ROS, ePAD from the current cardiac cycle can be substituted for ePAD from the subsequent beat. By substituting IST and ePAD from the current beat, all computations arise from the current cardiac cycle, simplifying the implementation.

The run-off slope 40 is applied over the integration time interval to compute an area A5 used to account for changes in pulmonary vascular resistance when estimating SV. The area A5 is computed as the area of a triangle 42 defined by the run-off slope 40 applied between the integration start time 42 and the corrected integration end time 36. The area A5 is computed from the following equation {5};

$$A5=0.5*\{(CIET-IST)*(ROS*(CIET-IST))\} \quad \{5\}$$

Another way of illustrating the effect of variations in pulmonary vascular resistance on SV estimated from the RVP waveform 10 is shown by the shaded region 44. Shaded region 44 is an area equal to triangular area 42 but is applied to the pulse contour of the RVP waveform 10 during the ejection phase, which is defined by the integration start time 28 and the corrected integration end time 36. The correction area A5 will increase as ROS 40 increases. A decrease in pulmonary vascular resistance will increase the computed ROS 40 due to a greater difference between MPAP and ePAD. With a decrease in pulmonary vascular resistance, greater forward flow may be produced by the developed RVP. Thus, the correction area A5 will be greater as ROS 40 increases representing an increase in forward flow as pulmonary vascular resistance decreases.

When pulmonary vascular resistance increases, the ROS slope 40 will decrease, decreasing the correction area A5. The decreased correction area A5 is analogous to a decrease in forward flow in response to developed RVP due to increased pulmonary vascular resistance. An overall estimated stroke volume will thus be corrected for changes in pulmonary vascular resistance by inclusion of A5 in the computation of the estimated stroke volume. In some embodiments, the area A5 or its contour may be used in computing ah estimated SV without additional computations of A1 through A4.

Figure 10:
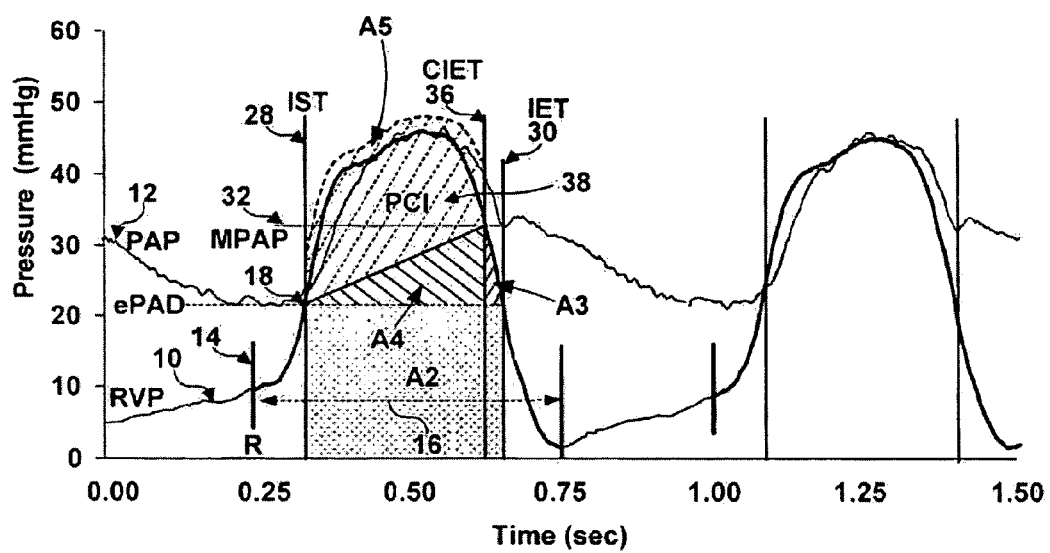
FIG. 10 illustrates the computation of a pulse contour integral (PCI) from the total area A1 under RVP waveform between integration start time and integration end time and the correction areas A2, A3, A4 and A5.

FIG. 10 illustrates the computation of a pulse contour integral (PCI) 38 from the total area A1 under RVP waveform 10 between integration start time 20 and integration end time 30 and the correction areas A2, A3, A4 and A5. PCI 38 is computed according to the following equation {6}:

$$PCI=A1-A2-bA3-cA4+dA5 \quad \{6\}$$

wherein the coefficients b, c and d may be 0 or 1 or determined to be another real or non-linear weighting factor based on experimental or clinical studies or individual patient results. The decision to activate or not activate correction areas A3, A4 and A5, e.g., using a value of 1 or 0 for the respective coefficients b, c, and d, may be made based on the type of medical condition. For example, conditions such as pulmonary hypertension, congestive heart failure, fast relaxation (lusitropic function), large heart rate range during data acquisition, or other medical conditions may be factors in determining the criteria for activating the correction areas A3, A4, and A5 in computing PCI 38 and determining the appropriate values for coefficients b, c, and d. The resulting area of PCI 38 is a useful estimate of stroke volume. When computed by an IMD processor, the stroke volume estimated as the PCI 38 is determined in digital units according to equation {6} above. This estimated stroke volume may be stored by the IMD and/or used in a closed-loop fashion for controlling IMD therapies. In lieu of or in addition to the foregoing, calibration data can be wirelessly downloaded to the IMD so that a memory structure of the IMD retains any preset thresholds (e.g., set by a clinician) to enhance therapy delivery.

Figure 11:
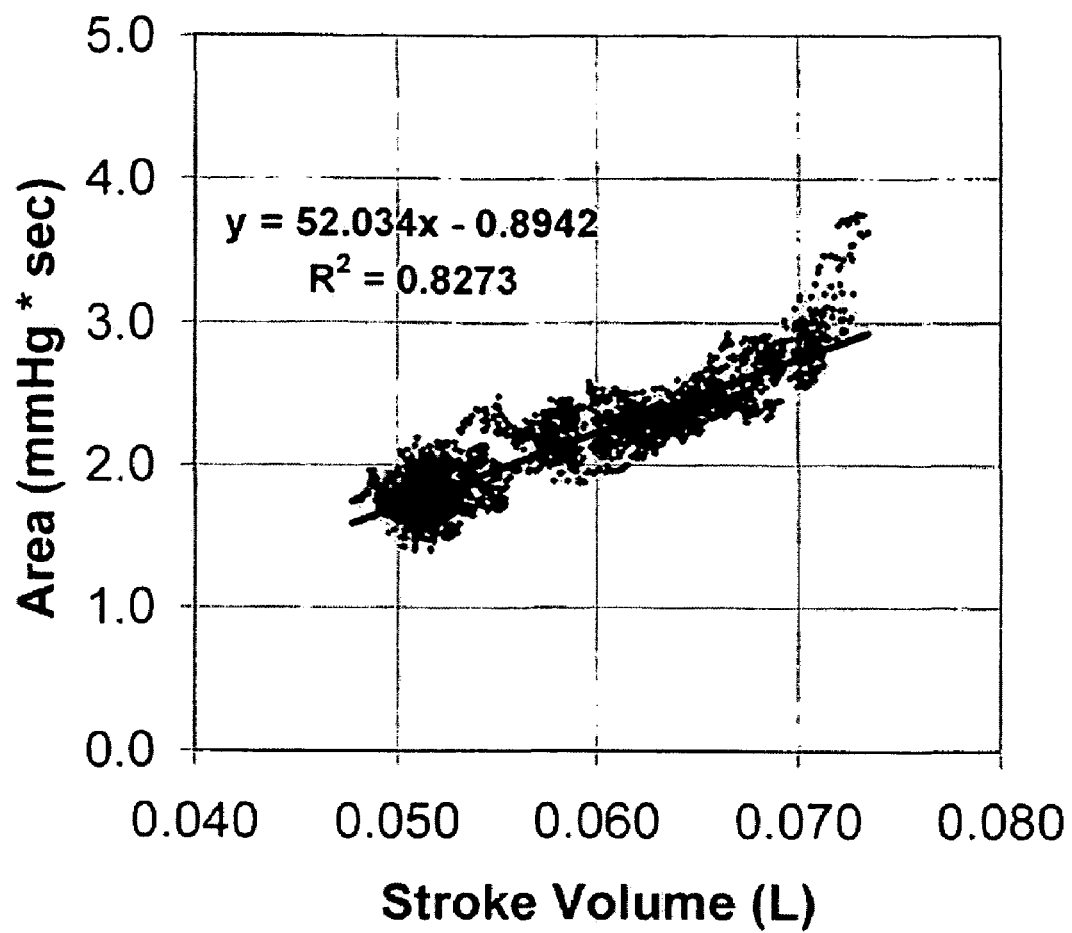
FIG. 11 is a plot of estimated SV computed using the RVP pulse contour method provided by the invention versus stroke volume measured by placing a flow probe on the pulmonary artery in a canine study.

FIG. 11 is a plot of estimated stroke volume computed using the RVP pulse contour method provided by the invention versus stroke volume measured by placing a flow probe on the pulmonary artery in a canine study (n=1). A strong correlation ($R^2$=0.83) is demonstrated between the estimated stroke volume (y-axis), computed as the PCI of the RVP waveform as described above, and the actual measured stroke volume (x-axis). Based on the linear relation between the computed PCI and the measured stroke volume, linear calibration factors, a gain and an offset, may be determined to convert the PCI in digital units to units of volume:

$$eSV(L)=gain*PCI+offset. \quad \{7\}$$

In the example shown in FIG. 11, the linear regression of PCI and measured stroke volume provides the following equation for computing an estimated stroke volume to units of volume from the PCI in digital units:

$$eSV(L)=0.019*PCI+0.017 \quad \{8\}$$

Figure 12:
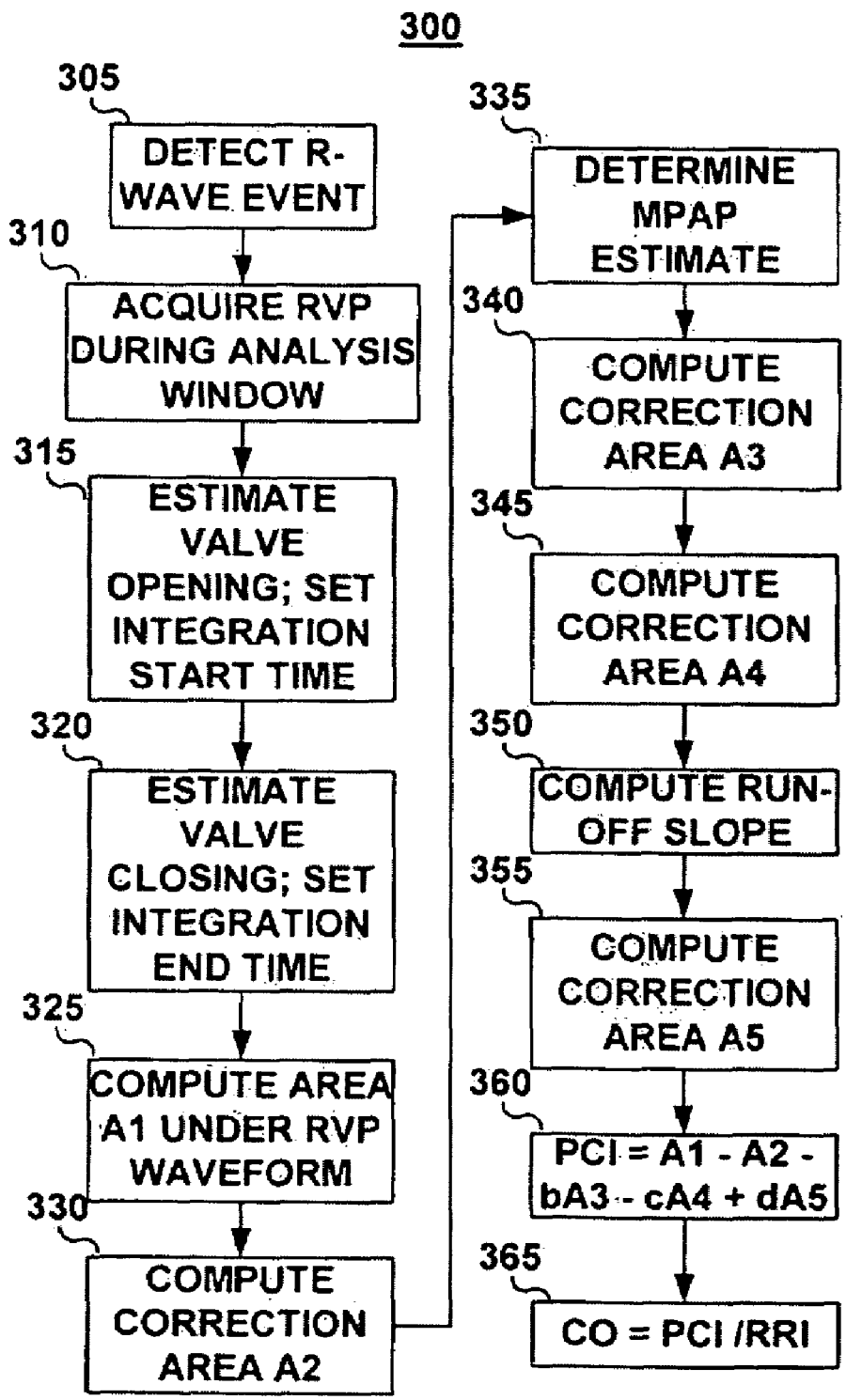
FIG. 12 is a flow chart summarizing the steps performed in a method for monitoring cardiac output using the RVP pulse contour method for estimating SV as described in conjunction with FIGS. 5 through 9.

FIG. 12 is a flow chart summarizing the steps performed in a method for monitoring cardiac output using the RVP pulse contour method for estimating stroke volume described in conjunction with FIGS. 5 through 9. At step 305, an R-wave or related event is detected to indicate the start of a cardiac cycle. Detection of an R-wave event sets the start of an analysis window during which the RV pressure signal is acquired and stored in a memory buffer at step 310. The analysis window is set to a duration that will include the systolic time interval or at least the ejection time interval.

At step 315, an integration start time is set based on an estimated time of pulmonic valve opening. In the method described above in conjunction with FIG. 5, the integration start time is set at the time that the RVP signal amplitude equals the estimated pulmonary artery diastolic pressure (ePAD), which corresponds to the maximum rate of RVP rise (dP/dt max). Other methods for estimating the time of pulmonic valve opening, including other methods that rely on alternative physiological signals, could be utilized in setting the integration start time (IST) at step 315. If the IST is illogical in its timing relative to an R-wave event detection the current cardiac cycle would be ignored.

At step 320, the integration end time (IET) is set based on an estimated time of pulmonic valve closure. In the method described above in conjunction with FIG. 5, the integration end time is set at the time that the falling RVP signal amplitude equals ePAD. Other methods for estimating pulmonic valve closure time could be utilized, including methods that rely on alternative physiological signals. For example, methods could be conceived that utilize acoustical signals for detecting the time of pulmonic valve opening and closure for setting an integration start and end time to be applied to the RVP signal at steps 315 and 320. If the IET is illogical in its timing relative to the IST, then the entire cardiac cycle would be ignored.

At step 325, the area A1 under the RVP waveform is determined by integrating the RVP signal over the time interval defined by the integration start time and integration end time. In some embodiments, the area A1 may be used as a measure of estimated stroke volume. However, a more sensitive and accurate estimate of stroke volume may be obtained by correcting the area A1 using a number of correction areas that are also computed by identifying selected features of the RVP waveform. Various logical criteria could be set up to ensure a valid range of values for A1. If the criteria were not met, the entire cardiac cycle would be ignored.

At step 330, correction area A2 is computed as the area under the estimated pulmonary artery diastolic pressure (ePAD) between the integration start time and integration end time. Various logical criteria could be set up to ensure a valid range of values for A2. If the criteria were not met, the entire cardiac cycle would be ignored.

At step 335, a mean pulmonary artery pressure (MPAP) estimate is determined from the RVP signal as described above; in conjunction with FIG. 7. The MPAP is used to set a corrected integration end time that occurs earlier than the integration end time set based on ePAD at step 320. A correction area A3 is computed at step 340 as the area under the RVP waveform between the corrected integration end time and the previously set integration end time. Area A3 may be approximated as a triangle. If the MPAP estimate corresponds to a corrected integration end time that occurs later in time than the integration end time set based on ePAD, the corrected integration end time is considered to be an anomalous result. The entire cardiac cycle is ignored if the corrected integration end time is later than IET due to the illogical condition of the estimated MPAP being less than ePAD.

At step 345, correction area A4 is computed based on the MPAP estimate and the corrected integration end time. Correction area A4 may be approximated as a triangle defined by ePAD, MPAP, and the integration start and end time as described previously in conjunction with FIG. 8.

At step 350 a run-off slope is computed as the slope between the MPAP and ePAD over the diastolic and pre-ejection intervals. The run-off slope is applied over the integration interval starting at the integration start time and ending at the corrected integration end time to compute a correction area A5 as described in conjunction with FIG. 9. Correction area A5 may be used to account for variations in pulmonary vascular resistance.

The pulse contour integral (PCI) is determined at step 360 from the computed areas A1, A2, A3, A4, and A5, wherein each area may be assigned coefficient or weighting factor. The PCI is an estimate of stroke volume for the given cardiac cycle. The PCI and the RRI measured for the current cardiac cycle is used to compute cardiac output at step 365 on a beat-by-beat basis. Cardiac output may also be determined on an averaged basis over multiple cardiac cycles, and beat-by-beat or averaged cardiac output measurements may be used to monitor trends in hemodynamic status of a patient. If the PCI value does not meet a set of predefined logical PCI range criteria, the current cardiac cycle is ignored.

Figure 13:
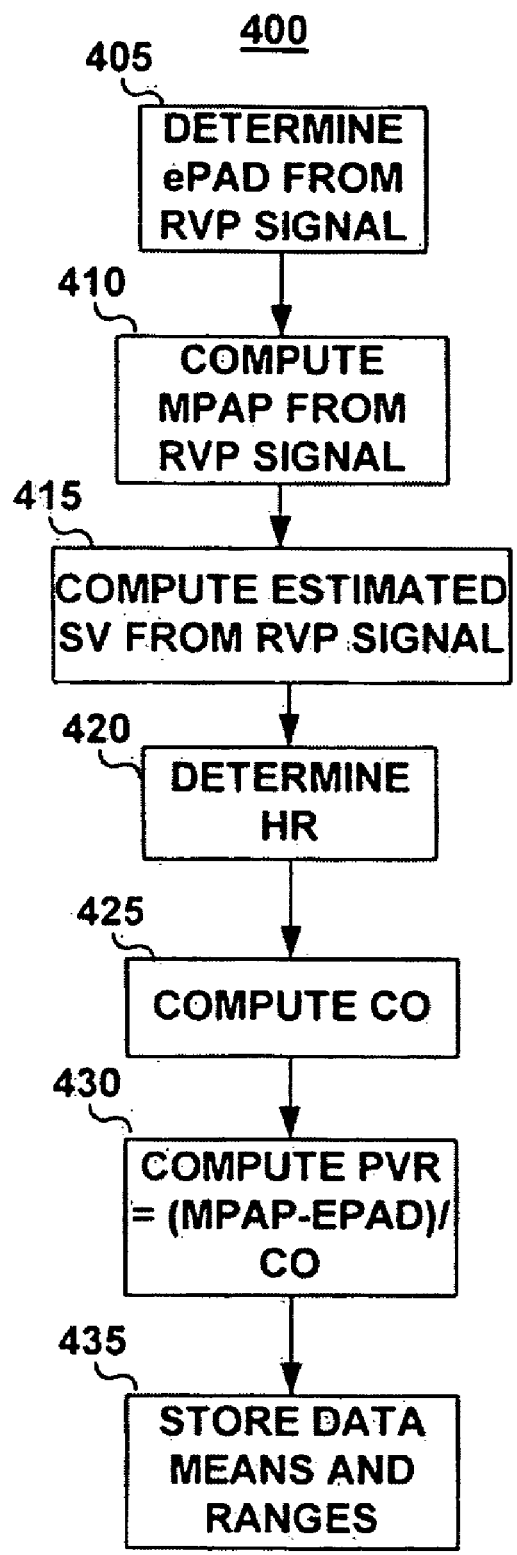
FIG. 13 is a flow chart summarizing a method for monitoring the hemodynamic status of a patient.

FIG. 13 is a flow chart summarizing a method for monitoring the hemodynamic status of a patient. Method 400 is executed by an IMD on a beat-by-beat basis to obtain pulmonary artery pressure data and cardiac output measures. Such data can be used to assess trends in hemodynamic status of patient with congestive heart failure, providing useful information for managing heart failure therapies.

At step 405, ePAD is determined from the RVP signal as the RVP amplitude at the time of the maximum dP/dt. At step 410, MPAP is estimated from the RVP signal according to the weighted average of the peak RVP and ePAD as described previously and as generally disclosed in the above-referenced U.S. patent application Ser. No. 09/997,753.

At step 415, the patient's stroke volume is estimated from the RVP signal based on a determination of landmark features of the RVP signal in accordance with the methods described above. At step 410 the heart rate (HR) is determined for use in computing a measure of CO from the estimated SV at step 415. For a beat-by-beat computation of CO, the estimated SV is divided by the RRI. In binary arithmetic, the SV/RRI quotient in digital units is multiplied by a conversion constant of 60000.

At step 430 a measure of pulmonary vascular resistance (PVR) is computed from the estimated CO (flow) and the estimated pulmonary artery pressures:

$$PVR = (MPAP - ePAD)/CO \quad \{9\}$$

At step 435, the ePAD, MPAP, estimated SV, computed CO and PVR values are stored. Data may be stored in a variety of formats including beat-by-beat data storage, histogram storage, or storage of statistical aspects of the beat-by-beat values. In the example shown in FIG. 13, a mean value and range (high and low) for each parameter measured during a monitoring episode of a series of cardiac beats is stored.

The pulmonary pressure and flow data derived from the RVP signal is made available to a clinician for further review or analysis by uplinking the stored data to an external device. The derived pressure and flow data is valuable in managing the treatment of congestive heart failure where the goal is to reduce filling pressures while maintaining adequate CO. The derived pressure and flow data can be uplinked in real-time to provide information to the clinician regarding the hemodynamic response to clinical interventions. The data can also be made available for use by the IMD in real-time, closed-loop therapy control algorithms responsive to relative changes in estimated SV or estimated CO.

The detailed embodiments described herein have referred primarily to the use of a RVP signal for estimating pulmonary artery pressures and right-side stroke volume there from. However, the methods described herein can be adapted for application to LVP signals wherein LVP signal features are selected for estimating aortic pressures and computing triangular or polygonal areas or computing a pulse contour integral for estimating left-sided flow. For example, an estimated aortic diastolic pressure may be derived as the LVP at dP/dt max and used as an integration start time. The time at which the descending portion of the LVP curve reaches the estimated aortic diastolic pressure may be used as an integration end time. A mean aortic pressure may be estimated from the LVP signal using a method analogous to the MPAP estimation method using the RVP signal for determining a corrected integration end time. Likewise, a number of correction areas could be defined and computed using various landmark pressure and time points selected from the LVP signal.

The invention provides a method and apparatus for hemodynamic monitoring based on ventricular pressure signals. Variations to the methods described herein may be conceived by one having skill in the art and the benefit of the teachings provided herein without departing from the scope of the invention. The embodiments described herein are intended to illustrate exemplary methods for practicing the invention and should not be interpreted as limiting with regard to the following claims.

What is claimed is:

1. A method, comprising:
sensing a cardiac electrogram (EGM) signal of the heart;
sensing a right ventricular pressure (RVP) signal;
computing an estimated stroke volume using the sensed EGM signal and the sensed RVP signal;
wherein computing an estimated stroke volume comprises computing a RVP pulse contour integral by:
identifying an integration start time corresponding to an estimated time of pulmonic valve opening;
identifying an integration end time corresponding to an estimated time of pulmonic valve closure;
computing the area under the right ventricular pressure signal between the integration start time and the integration end time; and
wherein computing the RVP pulse contour comprises computing a plurality of correction areas used to adjust the area under the right ventricular pressure signal between the integration start time and the integration end time; and
one of displaying and storing in a memory structure at least one of: the RVP pulse contour, the estimated stroke volume, the right ventricular pressure signal, the area.

2. A method according to claim 1 wherein sensing the right ventricular pressure signal further comprises:
detecting an R-wave event from the sensed EGM signal;
setting an analysis window for a predetermined interval of time following the R-wave event detection; and
acquiring and storing the RVP signal during the analysis window.

3. A method according to claim 1 wherein computing an estimated stroke volume further comprises:
deriving an estimated pulmonary artery diastolic pressure from the RVP signal;
deriving a peak right ventricular pressure amplitude from the RVP signal; and
computing a difference between the estimated pulmonary artery diastolic pressure and the peak right ventricular pressure amplitude.

4. A method according to claim 1 wherein the estimated time of pulmonic valve opening is a time corresponding to a maximum rate of pressure rise in the right ventricular pressure signal.

5. A method according to claim 1 wherein the estimated time of pulmonic valve closure is a time corresponding to a right ventricular pressure amplitude occurring on a descending portion of the right ventricular pressure signal and equaling a right ventricular pressure amplitude at the integration start time.

6. A method according to claim 1 wherein computing a plurality of correction areas comprises:
deriving an estimated pulmonary artery diastolic pressure using the right ventricular pressure signal and the EGM signal, and
computing the area below the estimated pulmonary artery diastolic pressure and between the integration start time and the integration end time.

7. A method according to claim 1 wherein computing a plurality of correction areas comprises:
deriving a mean pulmonary artery pressure using the RVP signal and the EGM signal;
identifying a corrected integration end time corresponding to a time that a RVP signal amplitude occurring on a descending portion of the right ventricular pressure signal equals the estimated mean pulmonary artery pressure; arid
computing an area under the right ventricular pressure signal between the corrected integration end time and the integration end time.

8. A method according to claim 1 wherein computing a plurality of correction areas comprises:
deriving a mean pulmonary artery pressure using the RVP signal and the EGM signal;
identifying a corrected integration end time corresponding to a time that a RVP signal amplitude occurring on a descending portion of the right ventricular pressure signal equals the estimated mean pulmonary artery pressure;
deriving an estimated pulmonary artery diastolic pressure using the right ventricular pressure signal and the EGM signal;
computing a triangular area having sides defined by a horizontal line corresponding to the estimated pulmonary artery diastolic pressure, a vertical line corresponding to the corrected integration end time, and a line segment intersecting the horizontal line at a point on a descending portion of the RVP signal equal in amplitude to the derived mean pulmonary artery pressure and intersecting the vertical line at a point on an ascending portion of the RVP signal equal to the estimated pulmonary artery diastolic pressure.

9. A method according to claim 1 wherein computing a plurality of correction areas comprises computing a correction area corresponding to changes in pulmonary vascular resistance.

10. A method according to claim 9 wherein computing a correction area corresponding to changes in pulmonary vascular resistance comprises:
deriving a mean pulmonary artery pressure using the RVP signal and the EGM signal;
identifying a corrected integration end time, corresponding to a time that a RVP signal amplitude occurring on a descending portion of the right ventricular pressure signal equals the estimated mean pulmonary artery pressure;
deriving an estimated pulmonary artery diastolic pressure using the right ventricular pressure signal and the EGM signal;
computing a slope between the mean pulmonary artery pressure and the estimated pulmonary artery diastolic pressure over a time interval derived from the EGM signal corresponding to a diastolic interval and pre-ejection interval;
computing the area of a triangle defined by the slope applied between the integration start time and the corrected integration end time.

11. A method according to claim 1 wherein computing the estimated stroke volume comprises computing the RVP pulse contour integral as a function of the area under the RVP curve between the integration start time and the integration end time and the plurality of correction areas.

12. A method according to claim 1 further comprising computing a cardiac output from the estimated stroke volume and a heart rate derived from the EGM signal.

13. A method according to claim 1 further comprising computing a cardiac output using the estimated stroke volume and a heart rate derived from the EGM signal.

14. A method for monitoring the hemodynamic status of a patient, comprising:
- sensing a cardiac electrogram (EGM) signal of the heart;
- sensing a right ventricular pressure (RVP) signal;
- computing an estimated stroke volume using the sensed EGM signal and the sensed RVP signal;
- deriving a mean pulmonary artery pressure using the RVP signal and the EGM signal; and
- deriving an estimated pulmonary artery diastolic pressure using the right ventricular pressure signal and the EGM signal; and
- computing a pulmonary vascular resistance using the sensed EGM signal and the sensed RVP signal;
- wherein computing a pulmonary vascular resistance comprises:
  - computing a pressure difference between the mean pulmonary artery pressure and the estimated pulmonary artery diastolic pressure;
  - computing a cardiac output metric using the estimated stroke volume and a heart rate derived from the EGM signal;
  - dividing the pressure difference by the cardiac output; and
  - one of displaying and storing in a memory structure at least one of: the cardiac output metric, the estimated stroke volume, the heart rate, the pressure difference, the pulmonary vascular resistance, the right ventricular pressure, the mean pulmonary, artery pressure, the estimated pulmonary artery diastolic pressure.

* * * * *

UNITED STATES PATENT AND TRADEMARK OFFICE
CERTIFICATE OF CORRECTION

| | | |
|---|---|---|
| PATENT NO. | : 7,507,208 B2 | Page 1 of 1 |
| APPLICATION NO. | : 12/124847 | |
| DATED | : March 24, 2009 | |
| INVENTOR(S) | : Tommy D. Bennett, Robert T. Taepke, II and Barbro M. Kjellstrom | |

It is certified that error appears in the above-identified patent and that said Letters Patent is hereby corrected as shown below:

Claim 7, Col. 16, line 5, delete "'; arid"
And insert in place thereof --; and--.

Claim 10, Col. 16, line 41, delete "time corresponding"
And insert in place thereof --time, corresponding--.

Signed and Sealed this

Third Day of November, 2009

David J. Kappos
*Director of the United States Patent and Trademark Office*